United States Patent [19]

Durham

[11] 4,235,923

[45] Nov. 25, 1980

[54] ESTERS OF 3-SUBSTITUTED-2-(AMINOCARBONYL)OXIRANECARBOXYLIC ACIDS AS LIPOGENESIS INHIBITORS

[75] Inventor: Harry G. Durham, Modesto, Calif.

[73] Assignee: Shell Oil Company, Houston, Tex.

[21] Appl. No.: 36,116

[22] Filed: May 4, 1979

Related U.S. Application Data

[63] Continuation-in-part of Ser. No. 926,368, Jul. 20, 1978, abandoned, which is a continuation of Ser. No. 784,097, Apr. 4, 1977, abandoned.

[51] Int. Cl.$^2$ .......................................... A61K 31/335
[52] U.S. Cl. .................................................. 424/278
[58] Field of Search ...................................... 424/278

Primary Examiner—Stanley J. Friedman

[57] ABSTRACT

Esters of 3-substituted-2-(aminocarbonyl)oxiranecarboxylic acids inhibit lipogenesis in mammals.

1 Claim, No Drawings

ESTERS OF 3-SUBSTITUTED-2-(AMINOCARBONYL)OXIRANECARBOXYLIC ACIDS AS LIPOGENESIS INHIBITORS

This application is a continuation-in-part of application Ser. No. 926,368, filed on July 20, 1978, now abandoned as a continuation of application Ser. No. 784,097, filed on Apr. 4, 1977, now abandoned.

DESCRIPTION OF THE INVENTION

It has been found that lipogenesis in mammals is inhibited by esters of 3-substituted-2-(aminocarbonyl)oxiranecarboxylic acids, such esters being described by the general formula:

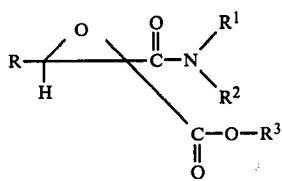

wherein R is alkyl, cycloalkyl, alkenyl, alkynyl, or cycloalkylalkyl, or is phenyl, or phenyl substituted by one or two of nitro, lower alkyl or alkoxy, or halogen, or is benzoyl, $R^3$ is alkyl, alkenyl, alkynyl or cycloalkyl, and $R^1$ and $R^2$ each is hydrogen, one of the moieties represented by $R^3$, or together represent $-(CH_2)_n-$, wherein n is four or five, which forms a hetero ring with the indicated nitrogen atom.

In these compounds, each alkyl, alkenyl and alkynyl moiety can be of straight-chain or branched-chain configuration, and of up to twenty carbon atoms, while each lower alkyl moiety contains from one to six carbon atoms. Each cycloalkyl moiety contains from three to six carbon atoms, while the "alkyl" portion of each cycloalkylalkyl moiety contains from one to six carbon atoms, with from one to two carbon atoms joining the cycloalkyl or phenyl moiety to the oxirane ring. Preferred halogen is chlorine.

Preferred of these compounds, because of their activity as lipogenesis inhibitors, are those wherein R is phenyl or substituted phenyl, or is alkyl of from four to twelve carbon atoms, $R^1$ and $R^2$ each is hydrogen and $R^3$ is alkyl of from one to four carbon atoms.

Compounds of the invention can exist as either of two geometrical (cis-trans) isomers, depending upon the spatial relationship of the moieties upon the oxirane ring. Further, chirality exists in the compounds due to the asymmetric configurations at the 2- and 3-positions of the oxirane ring. As a result, four optical isomers exist, one pair for each of the two geometrical isomers. Both the cis and trans isomer products, as prepared, have been found to inhibit lipogenesis. The individual optical isomers have not been separated, so that their respective activity as lipogenesis inhibitors has not been determined. In this specification, for the sake of simplicity, these compounds will be referred to generally as esters of 3-substituted-2-(aminocarbonyl)oxiranecarboxylic acids, this terminology including each of the isomers, as well as mixtures thereof. Under the circumstances, the invention contemplates each of the individual isomers, as well as mixtures thereof.

For illustration, preparation of typical individual species of the genus defined by formula (I) are described in the examples included hereinafter. Other typical, illustrative individual species of this genus are those wherein the symbols define the moieties:

$R^3$ is ethyl, $R^1$ and $R^2$ each is hydrogen, R is dodecyl;
$R^3$ is ethyl, $R^1$ and $R^2$ each is hydrogen, R is butyl;
$R^3$ is ethyl, $R^1$ is hydrogen, $R^2$ is isopropyl, R is 2,6-dichlorophenyl;
$R^3$ is 2-propenyl; $R_1=R_2=H$; R=4-chlorophenyl;
$R^3$ is 2-propynyl; $R_1=R_2=H$; R=phenyl;
$R^3$ is cyclohexyl; $R_1=R_2=H$; R=4-methylphenyl;
$R^3$ is ethyl; $R_1=H$; $R_2=$2-propenyl; R=phenyl;
$R^3$ is ethyl; $R_1=H$; $R_2=$2-propynyl; R=4-chlorophenyl;
$R^3$ is ethyl; $R_1=H$; $R_2=$cyclohexyl; R=octyl;
$R^3$ is butyl; $R_1+R_2=-(CH_2)_5-$; R=hexyl;
$R^3$ is propyl; $R_1=R_2=H$; R=2-pentenyl;
$R^3$ is ethyl; $R_1=R_2=H$; R=4-pentynyl;
$R_3$ is ethyl; $R_1=R_2=H$; R=cyclohexylmethyl.

The lipogenesis inhibitors of this invention are a known class of compounds, those wherein R is alkyl being disclosed by M. Igaroshi and H. Midorikawa, J. Org. Chem., 28, 3088-3092 (1963) (Reference I), while those wherein R is phenyl are disclosed by A. Robert and A. Foucaud, Bull. Soc. Chim. France, 1969, 2537-44 (Reference II). Compounds contemplated in the invention not specifically disclosed in those publications can be prepared by the methods disclosed therein.

The procedures for preparing compounds of Formula I are illustrated in Examples 1-16, following. In each case, the identity of the product and of any precursor involved were confirmed by appropriate chemical and spectral analyses.

EXAMPLE 1

Ethyl 2-(aminocarbonyl)-3-hexyloxiranecarboxylate trans (1)

1 was prepared as a white crystalline solid, mp: 86° C. (Reference I: 81°-82° C.), by the procedure of Reference I, using sodium tungstate dihydrate as catalyst.

EXAMPLE 2

Ethyl 2-(aminocarbonyl)-3-hexyloxiranecarboxylate cis (2)

A mixture of 31 g of diethyl heptylidenepropanedioate (B. Wojcik and H. Adkins, J. Am. Chem. Soc., 56, 2424 (1934), prepared by the method of A. C. Cope and K. E. Hoyle, J. Am. Chem. Soc., 63, 733 (1941)), 5 g of potassium bicarbonate and 17 g of 30% hydrogen peroxide in 200 ml of methanol was stirred for two hours at 40° C., then allowed to stand at 20° C. for 16 hours. The mixture then was concentrated to 50 ml; 100 ml of water was added and the solution was extracted with two 50-ml volumes of methylene chloride. The solvent was evaporated to give a colorless liquid, which was vacuum distilled to give diethyl 3-hexyloxiranedicarboxylate (2A), bp: 117°-126° C. at 0.1 Torr.

A solution of 8.0 g of 2A in 10 ml of ethanol was saturated with ammonia (gas) and the mixture was allowed to stand for 2 days at room temperature. The precipitate that formed was collected and recrystallized from pentane to give 2, as white crystals, mp: 58°-60° C.

EXAMPLE 3

Ethyl 2-(aminocarbonyl)-3-methyloxiranecarboxylate (3)

60 g of ethyl 2-cyano-2-butenoate (F.D. Popp et al., J. Org. Chem., 26, 2738–40 (1961)) and 2 g of sodium tungstate dihydrate were dissolved in 100 ml of ethanol. 30 ml of 30% hydrogen peroxide was added to the solution dropwise at 50° C. A vigorous exothermic reaction occurred and the mixture was cooled to maintan it below 70° C. When the reaction was complete, the solvent was evaporated and the residue, an oil, was extracted with hot cyclohexane. The residue was distilled to give ethyl 2-cyano-3-methyloxiranecarboxylic (3A), as a fraction boiling at 67°–68° C. at 0.1 Torr.

20 g of 3A, 2 g of sodium tungstate dihydrate and 2 g of trisodium phosphate were mixed with 30 ml of ethanol. 50 ml of 30% hydrogen peroxide was added over a 30-minute period to the stirred mixture at 55° C. and the mixture was stirred for 90 minutes while being warmed to 60° C. Then 35 ml of 30% hydrogen peroxide was added at 60° C., sufficient ethanol to make the mixing homogeneous was added and the mixture was stirred for 5 hours at 60° C. The solvent then was evaporated and the aqueous residue was extracted with methylene chloride. The solvent was evaporated from the separated extract and the residue was triturated with carbon tetrachloride to give a solid product, which upon recrystallization from carbon tetrachloride gave 3, as a white solid, mp: 139°–140° C.

EXAMPLE 4

Ethyl 2-(Aminocarbonyl)-3-cyclohexyloxiranecarboxylate (4)

A mixture of 56 g of cyclohexanecarboxaldehyde, 56.5 g of ethyl cyanoacetate, 1 g of piperidine and 100 ml of acetic acid was heated on a steam bath for 30 minutes. The acetic acid was stripped under reduced pressure. The residue was dissolved in 500 ml of pentane. The solution was extracted, successively, with water, sodium bicarbonate solution, and water. The pentane was evaporated under reduced pressure and the residue was distilled to give the ethyl ester of 2-cyano-3-cyclohexyl-2-propenoic acid (4A), bp: 120°–121° C. at 0.01 Torr.

100 ml of 30% hydrogen peroxide was added drop-by-drop to a solution of 21 g of 4A in 100 ml of ethanol at 65° C. in the presence of 3 g of sodium tungstate dihydrate, the temperature being allowed to rise to 70°–75° C. The mixture was held at that temperature for 4 hours, then was allowed to stand overnight. The solid was collected and washed with ethanol to give 4, mp: 160°–161° C.

EXAMPLE 5

Ethyl 2-(aminocarbonyl)-3-phenyloxiranecarboxylate (5)

5 was prepared as a white crystalline solid, mp: 150°–151° C. (Reference II: 152°–154° C.) by the procedure of Reference II.

EXAMPLE 6

Ethyl 2-(methylamino)carbonyl)-3-phenyloxiranecarboxylate (6)

50 g of benzylidenemalonic acid, diethyl ester, (E. H. Kroeker, et al., J. Am. Chem. Soc., 56, 1171–3 (1934)) and 10 ml of 10% aqueous sodium bicarbonate were mixed with 100 ml of ethanol. 42 ml of 30% hydrogen peroxide was added dropwise over a 5-hour period at 70° C. Then 30 ml of 30% hydrogen peroxide was added over a one-hour period at 60° C. 100 ml of ethanol was added and the mixture was stirred for 8 hours at 60° C. The solvent was evaporated and the residue was extracted with methylene chloride. The solvent was evaporated from the separated extract and the residue was distilled to give ethyl 2-(ethoxycarbonyl)-3-phenyloxiranecarboxylate (6A), as a fraction boiling at 178°–180° C. at 0.05 Torr.

12 g of 6A and 4 g of 40% aqueous methylamine were mixed and the mixture was warmed to 30° C. Then 2 g of ethanol was added and the mixture was allowed to stand for 105 minutes. The solvent was evaporated. The residue was poured into water and the oily layer which formed was separated and treated with ether to leave 6, as a white solid, mp: 102°–103° C.

EXAMPLE 7

1-Methylethyl 2-(aminocarbonyl)-3-phenyloxiranecarboxylate (7)

A mixture of 125 g of cyanoacetic acid, 170 ml of benzene, 140 ml of isopropyl alcohol and 5 g of Amberlite 1R 180 resin was refluxed for 7 hours while distilling off the azeotropic mixture of isopropyl alcohol, benzene and water. When no more water formed, the liquid phase was decanted from the resin and the remaining solvents were evaporated under reduced pressure. The residue was distilled to give isopropyl cyanoacetate (7A).

A mixture of 95 g of benzaldehyde, 114.3 g of 7A, 1 g of piperidine and 200 ml of acetic acid was heated on a steam bath for 1 hour. The acetic acid and unreacted benzaldehyde were distilled off, to 100° C./0.2 Torr. The residue was extracted with hot hexane; no residue was left. The solution was chilled, and the solid that formed was recrystallized from methanol to give the 1-methylethyl ester of 2-cyano-3-phenyl-2-propenoic acid (7B), mp: 72°–73° C.

20 ml of 30% hydrogen peroxide was added over a 5-minute period to a mixture of 21.5 g of 7B, 100 ml of isopropyl alcohol and 1 ml of 1 N sodium carbonate solution at 60° C. The mixture then was heated at 70° C. for 1 hour and the solvent was evaporated under reduced pressure. 100 ml of water was added to the residue and the mixture was extracted with methylene chloride. The extract was dried (Celite) and the solvent was evaporated under reduced pressure. The residue was triturated with warm pentane, and recrystallized from isopropyl alcohol and dried in a vacuum oven to give 7, mp: 118°–119° C.

EXAMPLE 8

Methyl 2-(aminocarbonyl)-3-phenyloxiranecarboxylate (8)

100 ml of 30% hydrogen peroxide was added over a 20-minute period to a stirred mixture of 67 g of 1-phenyl-2-cyano-2-(ethoxycarbonyl)-1,2-epoxyethane (Reference II), 400 ml of methanol, 20 g of tribasic sodium phosphate (hydrate) and 8 g of 18 crown 6 ether at 25° C. The temperature was allowed to rise to 50° C. during the addition. The mixture then was cooled to 45° C. and 150 ml of the hydrogen peroxide solution was added over a 10-minute period. The temperature rose to 48° C.

It was held there for one hour, then was raised to 60° C. and held there for 2 hours. The volatile materials were evaporated under reduced pressure. The residue was recrystallized from chloroform to give 8, mp: 175°–177° C.

EXAMPLES 9–15

By the techniques described in Examples 5–8, the following further individual species of the compounds of Formula I were prepared from the appropriate benzaldehyde. The species are identified in terms of Formula I, in all cases R and $R^1$ each being hydrogen, $R^3$ being ethyl, and R being phenyl substituted by $R^0$ at the position on the ring indicated:

| Example No. | Compound No. | R° | Melting Point (°C.) |
|---|---|---|---|
| 9 | 9 | 4-chloro | 160–161 |
| 10 | 10 | 4-methyl | 139–140 |
| 11 | 11 | 3,4-dimethoxy | 177–178 |
| 12 | 12 | 3-nitro | 177–179 |
| 13 | 13 | 3,4-dichloro | 171–172 |
| 14 | 14 | 4-methoxy | 140–141 |
| 15 | 15 | 4-nitro | 191–194 |

EXAMPLE 16

Ethyl 2-(aminocarbonyl)-3-benzoyloxiranecarboxylate (16)

10 g of sodium was dissolved in 200 ml of ethanol. The solution was cooled to 30° C. and 45.2 g of ethyl cyanoacetate was added rapidly. The resulting mixture was cooled to −15° C. and stirred while a warm solution of 62 g of 2-chloroacetophenone in 100 ml of toluene was added over a 15-minute period, with cooling, allowing the temperature of the mixture to rise to 20° C. over a 1-hour period. The mixture was poured in ice/3 N hydrochloric acid, the organic phase was separated, the solvent was evaporated under reduced pressure and the residue was distilled under reduced pressure to give a liquid, bp: 130°–160° C., at 0.01 Torr., which solidified on standing. Recrystallization from cold ether gave the ethyl ester of 2-cyano-4-oxo-4-phenylbutanoic acid (16A), mp: 53°–54° C.

A mixture of 11.5 g of 16A, 5.5 g of selenium dioxide and 30 ml of chlorobenzene was refluxed at 135° C. Then the chlorobenzene was distilled off under reduced pressure. The residue was extracted with hot hexane. The hexane was evaporated from the extract under reduced pressure. 30 ml of chlorobenzene was added to the residue and the mixture was refluxed overnight. The chlorobenzene was evaporated under reduced pressure. The residue was extracted with ether. The extract was cooled to give a solid, which was recrystallized from hexane to give the E-isomer of the ethyl ester of 2-cyano-4-oxo-4-phenyl-2-butenoic acid (16B) mp: 74°–75° C.

A mixture of 10 g of 16B, 100 ml of ethanol, 2 g of tribasic sodium phosphate (hydrate) and 15 ml of 30% hydrogen peroxide solution was heated at 60° C. for 2 hours, then concentrated under reduced pressure. The residue was dissolved in methylene chloride. The solution was washed with water, concentrated to 25 ml and filtered. The solid was recrystallized from acetone to give 16, mp: 148°–149° C.

Compounds of Formula I have been found to inhibit lipogenesis in tissues of mammals. The manner in which they cause this effect is not known with certainty; it is believed that they interfere with the synthesis of fatty acids in the tissues. Their effectiveness for this purpose has been ascertained by immersing samples of swine adipose tissue in a liquid medium containing radioactive glucose and the test chemical, for a period of time, then isolating the lipid from the treated tissue and determining the incorporation of the radioactive carbon into lipid by means of scintillation counting techniques. These tests were conducted in swine adipose tissue because in swine, the primary site of lipogensis—i.e., fatty acid synthesis—appears to be adipose tissue.

Described in more detail, the tests were conducted according to the following general procedure:

150 milligrams of slices of swine adipose tissue were incubated at 37° C. for 2 hours with shaking in 3 milliliters of Krebs-Ringer bicarbonate solution containing one-half the normal calcium ion concentration, 60 micromoles of glucose, 0.5 micro-Curie of glucose-U$^{14}$C, and 300 microunits of insulin, and 5% dimethyl sulfoxide (DMSO). The test compounds were added as suspensions or solutions in DMSO and were present at a concentration of 100 micrograms per milliliter of the incubation mixture.

The incubation was terminated by addition of 0.25 milliliter of 1 N sulfuric acid. The resulting mixture was extracted with a total of 25 milliliters of chloroform: methanol (2:1 v/v). The extracts were washed according to Folch et al. (J. Biol. Chem., 226, 497–509, (1957)), air dried, and counted in a liquid scintillation counter with 15 milliliters of counting fluid (two parts toluene containing 0.4% w/v New England Nuclear Omnifluor: 1 part Triton X-100). The tests were conducted in triplicate and were accompanied by control tests in which all ingredients, proportions and conditions were the same except that no test compound was included. From the data obtained were calculated the percent inhibition of lipid synthesis by the test compound in each case. The data obtained from the tests are set out in Table 1, as the percent inhibition of lipogenesis compared to the results obtained in the control tests wherein only the test compound was omitted.

TABLE 1

| Compound No. | Percent Inhibition |
|---|---|
| 1 | 88 |
| 2 | 83 |
| 3 | 18 |
| 4 | 75 |
| 5 | 85 |
| 6 | 27 |
| 7 | 48 |
| 8 | 47 |
| 9 | 65 |
| 10 | 37 |
| 11 | 33 |
| 12 | 76 |
| 13 | 87 |
| 14 | 55 |
| 15 | 37 |
| 16 | 74 |

The esters of Formula I can be used to control lipogensis in warm-blooded animals such as, for example, pets, animals in a zoo, livestock, fur-bearing animals and domestic animals, including, but not limited to dogs, cats, mink, sheep, goats, swine, cattle, horses, mules and donkeys. The effect is obtained by administering an effective amount of one or a mixture of two or more of the esters orally or parenterally to the animal. They may be administered as such, or as an active ingredient of a conventional pharmaceutical formulation. They may be administered orally by any convenient means. Thus, they may be orally administered as a drench, by intubation, in the animal's food and water, in a food supplement or in a formulation expressly designed for administration of the drug. Suitable formulations include solutions, suspensions, dispersions, emulsions, tablets, boluses, powders, granules, capsules, syrups and elixirs. For parental administration, they may be in the form of a solution, suspension, dispersion or emulsion. They can be administered in the form of an implant or other controlled sustained release formulation. Inert carriers, such as one or more of water, edible oil, gelatin, lactose, starch, magnesium sterate, talc or vegetable gum can be used. The dosage of the ester needed to inhibit lipogenesis will depend upon the particular ester used, and the particular animal being treated. However, in general, satisfactory results are obtained when the esters are administered in a dosage of from about 1 to about 400 milligrams per kilogram of the animal's body weight. The ester can be administered in a single dose or in a series of doses in the same day, or over a period of days. For any particular animal, a specific dosage regimen should be adjusted according to the individual need, the particular ester(s) used as the inhibitor, and the professional judgement of the person administering or supervising the administration of the inhibitor. It is to be understood that the dosages set forth herein are exemplary only, and that they do not, to any extent, limit the scope or practice of the invention.

What is claimed is:

1. A method of inhibiting lipogenesis in a mammal, which comprises administering, to a mammal in need of such treatment, orally or parenterally an effective amount of a compound of the formula:

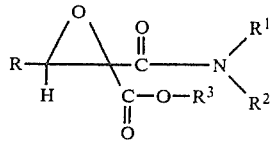

wherein R is alkyl, cycloalkyl, alkenyl, alkynyl, or cycloalkylalkyl, or is phenyl, or phenyl substituted by one or two of nitro, lower alkyl or alkoxy, or halogen, or is benzoyl, $R^3$ is alkyl, alkenyl, alkynyl or cycloalkyl, and $R^1$ and $R^2$ each is hydrogen, one of the moieties represented by $R^3$.

* * * * *